(12) United States Patent
Tridandapani et al.

(10) Patent No.: US 9,355,309 B2
(45) Date of Patent: May 31, 2016

(54) GENERATION OF MEDICAL IMAGE SERIES INCLUDING A PATIENT PHOTOGRAPH

(71) Applicants: EMORY UNIVERSITY, Atlanta, GA (US); GEORGIA TECH RESEARCH CORPORATION, Atlanta, GA (US)

(72) Inventors: Srini Tridandapani, Atlanta, GA (US); James Provenzale, Chapel Hill, NC (US); Mo Salama, Decatur, GA (US); Senthil Ramamurthy, Atlanta, GA (US); Pamela Bhatti, Atlanta, GA (US)

(73) Assignees: Emory University, Atlanta, GA (US); Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 13/736,334

(22) Filed: Jan. 8, 2013

(65) Prior Publication Data

US 2013/0177222 A1 Jul. 11, 2013

Related U.S. Application Data

(60) Provisional application No. 61/584,403, filed on Jan. 9, 2012.

(51) Int. Cl.
*G06K 9/00* (2006.01)
*A61B 5/117* (2016.01)
*G06F 19/00* (2011.01)

(52) U.S. Cl.
CPC .......... *G06K 9/00362* (2013.01); *A61B 5/117* (2013.01); *G06F 19/321* (2013.01); *G06F 19/322* (2013.01); *G06F 19/323* (2013.01); *G06F 19/3418* (2013.01)

(58) Field of Classification Search
None
See application file for complete search history.

(56) References Cited

U.S. PATENT DOCUMENTS

| | | | |
|---|---|---|---|
| 6,556,698 B1 | 4/2003 | Diano et al. | |
| 6,678,764 B2 * | 1/2004 | Parvulescu et al. | 710/65 |
| 7,278,027 B1 | 10/2007 | Todaka et al. | |
| 7,494,045 B2 | 2/2009 | Menhardt et al. | |
| 7,680,308 B2 | 3/2010 | Dale | |
| 7,731,683 B2 | 6/2010 | Jang et al. | |
| 7,764,765 B2 | 7/2010 | Ohta et al. | |
| 7,787,699 B2 | 8/2010 | Mahesh et al. | |
| 7,986,227 B2 | 7/2011 | Yankelevitz et al. | |
| 2005/0267351 A1 | 12/2005 | Humphrey et al. | |
| 2007/0076929 A1 | 4/2007 | Gentles et al. | |
| 2008/0219524 A1 * | 9/2008 | Brackett | 382/128 |
| 2009/0136094 A1 | 5/2009 | Driver et al. | |
| 2009/0141138 A1 * | 6/2009 | DeAngelis | 348/220.1 |
| 2010/0177013 A1 * | 7/2010 | Wirth et al. | 343/893 |
| 2010/0211409 A1 * | 8/2010 | Kotula et al. | 705/3 |
| 2010/0226550 A1 | 9/2010 | Miyasa et al. | |
| 2011/0002515 A1 * | 1/2011 | Futami et al. | 382/128 |
| 2011/0075803 A1 | 3/2011 | Zhu et al. | |
| 2011/0087664 A1 | 4/2011 | Westin et al. | |

OTHER PUBLICATIONS

By Dina Kraft "Radiologist Adds a Human Touch: Photos", Apr. 7, 2008, New York Times.*

(Continued)

*Primary Examiner* — Siamak Harandi
(74) *Attorney, Agent, or Firm* — Emory Patent Group

(57) ABSTRACT

Systems, methods, and computer-readable storage media relate to generate an image series that includes a patient image and a medical image. The patient image and the medical image may be associated based on identification information.

20 Claims, 9 Drawing Sheets

(56) References Cited

OTHER PUBLICATIONS

RSNA Press Release "Patient Photos Spur Radiologist Empathy and Eye for Detail", Dec. 2, 2008.*

I. Akel et al. "Surgery: Researchers at Hacettepe University, Department of Orthopedic Surgery Target Surgery in Adolescents", Apr. 11, 2008, Drug week, 1803, two pages.*

* cited by examiner

GENERATION OF MEDICAL IMAGE SERIES INCLUDING A PATIENT PHOTOGRAPH

CROSS REFERENCE TO RELATED APPLICATION

This application claims priority to U.S. Provisional Application Ser. No. 61/584,403 filed on Jan. 9, 2012, which is hereby incorporated by this reference in its entirety.

ACKNOWLEDGEMENT

This invention was made with government support under Grant IK23EB013221-01 awarded by the National Institutes of Health. The government has certain rights in the invention.

BACKGROUND

Medical errors and patient safety issues have gained prominence in the national dialogue on healthcare in the United States, particularly, since the publication of the 2000 and 2001 Institute of Medicine's reports on quality. Medical imaging studies are prone to mislabeling, such as associating the wrong demographic information (e.g., a different patient's name and medical record number (MRN)) to a patient's imaging examination. Patient misidentification errors in medical imaging can result in serious consequences. An error in the association of a medical image study and patient identification may propagate to future image studies and negatively affect patient management decisions.

The current acceptable protocol recommended by the Joint Commission involves the verification of at least two identifiers (e.g., name, date of birth, social security number or some hospital registration number) when the image is obtained.

SUMMARY

However, such verification may not be possible in some cases, such as trauma patients, patients who are unconscious and infants. Furthermore, even when the technologist correctly identifies the patient, incorrect entry of identifiers on imaging studies can occur for a variety of reasons, such as misidentification or mislabeling errors by a technologist or technician performing an imaging study at the point-of-care. Thus, there is a need to minimize or prevent mislabeling of medical imaging studies.

This disclosure generally relates to methods, systems, and computer readable storage media that include instructions for generating an integrated image series that includes at least one image (also referred to as "patient image") of a patient and at least one medical image of a patient. This series can be generated at the time the medical image is obtained, i.e., at the point-of-care. The methods, systems, and computer readable storage media according to the disclosure can (1) minimize the risk of or prevent the application of incorrect patient identification at the time of medical image generation, (2) allow the correlation of serial imaging studies by ensuring that all studies are from the same patient, and (3) prevent the generation of incorrect report. The methods, systems, and computer readable storage media according to the disclosure thus can minimize or prevent the risk of wrong treatment due to incorrect patient identification.

In some embodiments, the methods may comprise the steps of: receiving at least one patient image of a patient; receiving identification information; receiving at least one medical image of a patient; associating the patient image and the medical image based on the identification information; and generating an image series that includes the patient image and the medical image. In some embodiments, the generated image series may be associated with a medical record. In some embodiments, at least one patient image may be obtained simultaneously or substantially at the same time as the medical image.

In some embodiments, the method may further include confirming the patient of the patient image before obtaining the medical image. In some embodiments, the confirming may include comparing the patient of the patient image to another patient image or reference patient image associated with the medical record or work list. In some embodiments, the comparing may be based on patient information. In some embodiments, the method may include receiving at least one piece of patient information from a modality work list. In some embodiments, the method may include obtaining a reference patient image or another patient image based on the patient information and/or modality work list.

In some embodiments, the comparing may include comparing at least one physical characteristic of the patient of the patient image with at least one physical characteristic of a patient of another patient image and/or reference patient image. In some embodiments, the comparing may include extracting the physical characteristic of the patient of the patient image and the physical characteristic of the patient of the other patient image and/or the reference patient image. In other embodiments, the physical characteristic may include a physical feature, a facial feature, or an anatomic or physiologic landmark of the patient.

In some embodiments, the patient image may be static or dynamic. In some embodiments, the patient image may be a photograph or a video. In some embodiments the image may be a digital photograph or a digital video. In some embodiments, the method may further include converting the image of the patient from a first file format to a second file format. In some embodiments, the first file format may be a file format for a digital photograph or a digital video. In some embodiments, the first file format may be any one or more of JPEG, TIFF, PNG, GIF, BMP, WAV, AVI, FLV, MJ2, MPEG, MPEG-2, MP4, or QTFF. In some embodiments, the second file format may be a Digital Imaging and Communications in Medicine (DICOM) format.

In some embodiments, the medical image of a patient may be a medical image study. In some embodiments, the medical image may be generated by one or more medical imaging techniques. The medical imaging technique may be any known medical imaging modality. The medical imaging technique may include but is not limited to radiography, Computed Tomography (CT), ultrasound (US), magnetic resonance imaging (MRI), scintigraphy, mammography, single-photon emission computed tomography (SPECT) and positron-emission-tomography (PET) techniques. In some embodiments, the medical image may be generated by any known medical imaging device and system. The medical imaging devices or systems may include but are not limited to x-ray, MRI, UT, PET, CT, SPET, mammography, scintigraphy (such as scintillation cameras) or any known medical imaging devices or systems.

In some embodiments, the method may further include converting the medical image to a DICOM format. In some embodiments, the converting may include adding the identification information to the medical image.

The identification information may include at least one of an identifier for a recording device that records the medical image, an identifier for a medical imaging device or system that produces the medical image, acquisition time, image information, image practitioner information, and patient information. In some embodiments, the identification information may be included in a DICOM object. In some embodiments, the recording device may be any one or more of an imaging plate, an imaging film, a computer-readable storage medium, or any known recording device on which a medical image may be initially recorded. The image information may include attributes of the medical image (e.g., pixel data). The acquisition time may be at least one of date or time at which the medical image was obtained. The acquisition time may be in the form of a timestamp.

In some embodiments, at least one of the medical image, the identification information, or the image of the patient may be received over a wired network. In some embodiments, at least one of the medical image, the identification information, or the patient image may be received over a wireless network. In some embodiments, the wireless networks may be encrypted. The wireless network may include a wireless wide area network, a wireless local area network, a Bluetooth network, and a radio frequency network.

In some embodiments, the networks over which the medical image, the identification information, and the patient image are transmitted or received may be the same network. In some embodiments, the networks over which the medical image, the identification information, and the patient image are transmitted or received may be different networks.

In some embodiments, the method may include receiving a plurality of different medical images based on the identification information. In some embodiments, the identification information for each of the plurality of medical images may also be received. The plurality of different medical images and corresponding identification information may be obtained from a storage system. In some embodiments, the storage system may be a picture archiving and communication system (PACS). In some embodiments, the method may further include comparing the received medical images to the patient image.

In some embodiments, the identification information for each of the medical images may be compared to the identification information from the patient image.

In some embodiments, the method may further include confirming that the image series and the patient are properly associated. The method may further include comparing the patient image of the image series to another patient image. In some embodiments, the comparing may be based on another patient image associated with the medical record and/or patient information. In some embodiments, the comparing may be based on another medical image associated with the medical record. In further embodiments, the comparing may be based on patient information. In some embodiments, the comparing may be based on a reference patient image associated with the patient information. In some embodiments, the method may include obtaining another patient image or a reference patient image associated with the medical record of the patient of the patient image. In some embodiments, the method may include obtaining a reference patient image or another patient image based on the patient information and/or modality work list.

In some embodiments, the comparing may include comparing at least one physical characteristic of the patient of the patient image with at least one physical characteristic of a patient of another patient image and/or reference patient image. In some embodiments, the comparing may include extracting the physical characteristic of the patient of the patient image and the physical characteristic the patient of the other patient image and/or the reference patient image. In other embodiments, the physical characteristic may include a physical feature, a facial feature, or an anatomic or physiologic landmark of the patient.

In some embodiments, based on the comparing, the method may further include transmitting a prompt indicating a possibility that the patient of the patient image may not correspond to the patient associated with the patient information and/or medical record. In some embodiments, the prompt may be at least one of a visual alarm or an audible alarm.

In some embodiments, after the generating, the method may further include storing the image series on a storage system. The method may further include associating the image series with an electronic medical record for the patient.

In some embodiments, after the generating, the method may further include printing the image series. In some embodiments, the method may further include displaying the image series. In some embodiments, the method may further include transmitting an image series. In some embodiments, the transmitting may occur over a wireless network or wired network.

In some embodiments, a computer-readable storage medium may store instructions for generating an image series, the instructions may include receiving at least one patient image of a patient; receiving identification information; receiving at least one medical image of a patient; associating the patient image and the medical image based on the identification information; and generating an image series that includes the patient image and the medical image. In some embodiments, the generated image series may be associated with a medical record. In some embodiments, at least one patient image may be obtained simultaneously or substantially at the same time as the medical image.

In some embodiments, a system for generating an image series may include: a patient imaging device configured to obtain at least one patient image of a patient; a medical imaging device configured to obtain a medical image of a patient; an identification information device configured to obtain identification information; and an image series generation device configured to associate the patient image and the medical image based on at least one of the identification information and the patient image, and to generate an image series including the patient image and the medical image. In some embodiments, the patient imaging device may include a camera configured for at least one of still or dynamic images. In some embodiments, the medical imaging device may include any one of a radiography, Computed Tomography (CT), ultrasound (US), magnetic resonance imaging (MRI), scintigraphy, mammography, single-photon emission computed tomography (SPECT), endoscopy, and positron-emission-tomography (PET) device or system.

In some embodiments, the identification information device may include a camera configured for at least one of still or dynamic images. In some embodiments, the identification information device may be a radiofrequency identification (RFID) reader. In other embodiments, the identification information device may be configured to communicate with an identification information module to obtain the identification information. The identification information device may include a (radiofrequency) RF transceiver. In some embodiments, the patient identification information device may be integrated with the patient imaging device.

In some embodiments, the patient imaging device and the medical imaging device may be controlled so that the patient image and the medical image are obtained simultaneously or about the same time.

In some embodiments, the patient imaging device may be connected to the medical imaging device by a wireless network. The wireless network may be encrypted. The wireless network may include any one of a wireless wide area network, a wireless local area network, a Bluetooth network, or a radio frequency network.

Additional advantages of the disclosure will be series forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1A:
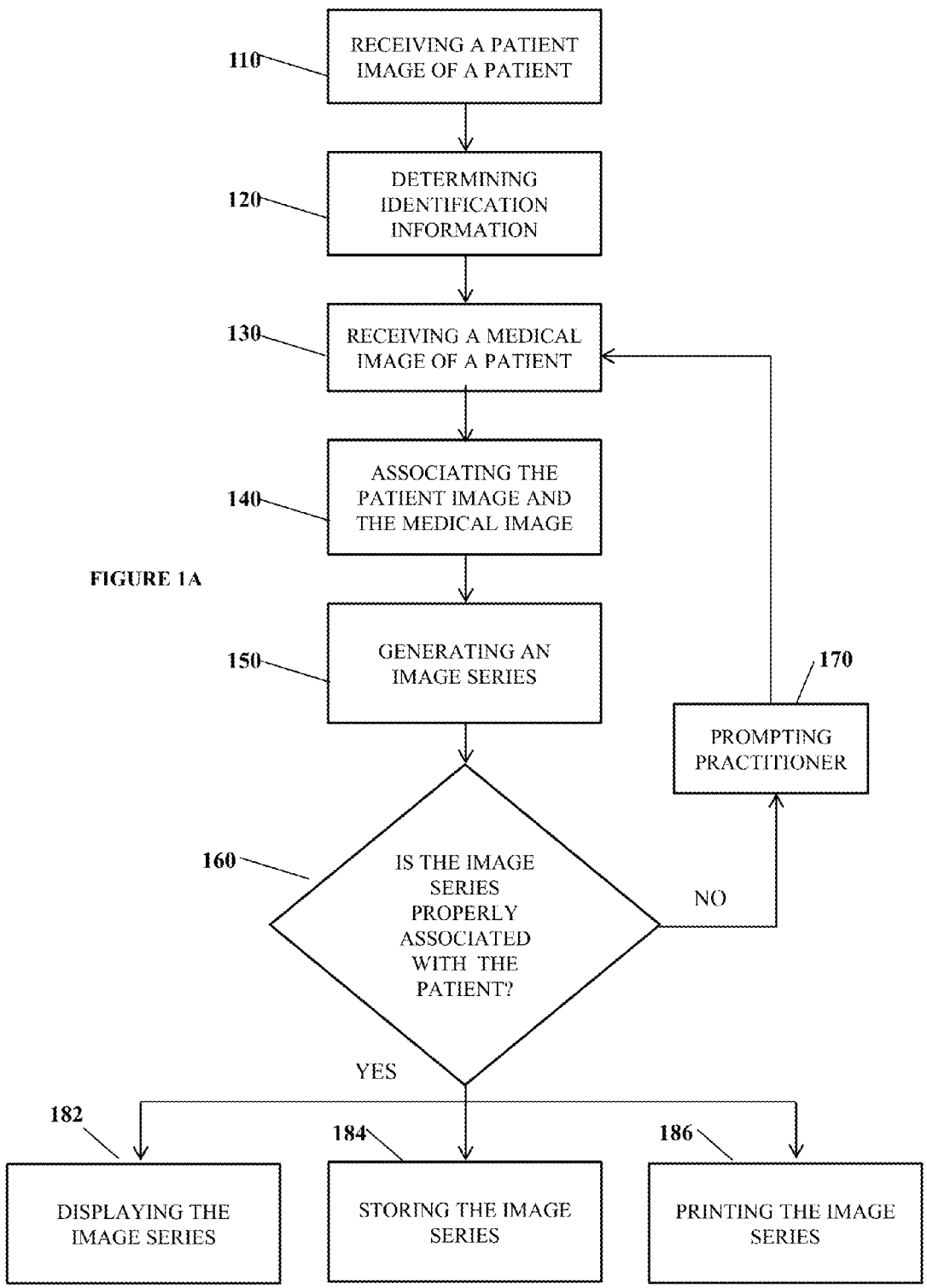
FIG. 1A illustrates a method according to embodiments for generating an image series that includes at least one patient image and at least one medical image.

The following description, numerous specific details are series forth such as examples of specific components, devices, methods, etc., in order to provide an understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

This disclosure generally relates to methods, systems, and computer readable storage media that include instructions for generating an image series that includes at least one patient image and at least one medical image.

The methods, systems, and computer readable storage media according to embodiments generate an image series that can form a powerful component of the patient demographic information associated with the medical image (or medical image study) thus decreasing and preventing medical errors. Wrong demographic information (e.g., a different patient's name and medical record number (MRN)) associated to a patient's imaging examination is a major cause of errors in medical imaging. The methods, systems and computer-readable storage media according to embodiments can address the mislabeled cases for which it is unlikely the radiologist would identify at the time of interpretation, such as, by comparing a current study with an older study purporting to be the same individual. For example, the methods, systems and computer-readable storage media according to embodiments address the cases for which two imaged individuals have similar physiques, an imaged individual has no or few anatomic or physiologic landmarks (e.g., pattern of bone islands, old fractures, or presence or pattern of surgical clips), and an imaged individual who has a similar last name as another imaged individual who arrived the same day at the imaging center. Generation of an image series that includes at least one patient image of a patient and the medical image of that purported patient, as well as a comparison of the images, will increase the detection rate of mislabeled studies, thereby decreasing medical errors. Further, this additional information in the patient image will also increase the interpreting physician's efficiency and throughput.

The methods, systems, and computer readable storage media according to embodiments generate an image series that also provides important supplemental information that can improve the diagnostic capabilities and value of a medical image study. A patient image of the patient may clarify ambiguities in the medical image, such as whether many medical lines and/or tubes shown in the medical image as projecting over the patient are outside or inside the patient. A patient image of the patient may show external or internal assist devices. Also, a patient image may show whether medical lines and/or tubes, such as nasogastric tubes, orogastric tubes, or endotracheal tubes, are present or absent. Such additional information can dramatically speed up the interpretation. This information is particularly useful when standing orders for the medical image include a generic indication, such as "check lines and tubes." Additionally, with respect to trauma imaging, a patient image of the patient may show the affected region, such as the entry and exit wounds of gun-shot victims or the presence of objects that protrude outside the patient. This information would further aid in the diagnostic accuracy of the medical imaging examinations by calling attention to these entities.

Further, the patient image may be useful for reducing radiation dosage by serving as a scout image for cross-sectional studies, such as CT. These photographic scouts may be used to limit the coverage extent of the cross-sectional slice acquisition. For example, with systems in which the digital cameras are spatially co-registered with the CT scanning equipment, it may be possible to avoid currently used scout/localizer images that require ionizing radiation.

As used herein, a patient image of a patient according to some embodiments may be one patient image of a patient. In other embodiments, the image of the patient may be a plurality of different images of the patient.

In some embodiments, the patient image may be a portrait of the patient. The patient image may be of any portion of a patient's body. In some embodiments, the patient image may be confined to the face of a patient, from about the forehead to the chin. In other embodiments, the patient image may include additional portions of a patient's body. In some embodiments, the image patient may also include upper chest area. In other embodiments, the patient image may include the area of the patient for which the medical image is obtained.

In some embodiments, the patient image may be still or dynamic. In some embodiments, the patient image may be a photograph or a video. In some embodiments, the patient image may be a digital photograph or a digital video.

In some embodiments, the patient image may be in any known digital format. In some embodiments, the format may be any one of JPEG, TIFF, PNG, GIF, BMP, WAV, AVI, FLV, MJ2, MPEG, MPEG-2, MP4, or QTFF. In some embodiments, the file format may be according to standards for transmitting radiological or other medical information, such as DICOM. In some embodiments, if the patient image is obtained in a format other than the format of the medical record storing system such as DICOM, the patient image may be later converted.

The format of the patient image may depend on the medical imaging device configuration. In some embodiments, a patient imaging device configured to obtain a still or dynamic patient image of the patient may be integrated with the medical imaging device. In other embodiments, a patient imaging device configured to obtain a still or dynamic image of the patient may be a peripheral device. In some embodiments, the patient image may be obtained by a video camera. In other embodiments, the patient image may be obtained by a digital camera. In some embodiments, the patient image may be obtained by a charge-coupled device or a complementary metal oxide semiconductor (CMOS) camera.

As used herein, a medical image of a patient, in some embodiments, may be one medical image. In other embodiments, a medical image of a patient may be more than one medical image. In some embodiments, a medical image of a patient may be an image study of that patient.

In some embodiments, the medical image may be generated by one or more medical imaging modalities. The medical imaging modality may be any known medical imaging modality or combination of modalities. The medical imaging modality may include but is not limited to radiography, Computed Tomography (CT), ultrasound (US), magnetic resonance imaging (MRI), scintigraphy, mammography, single-photon emission computed tomography (SPET), endoscopy, and positron-emission-tomography (PET). In some embodiments, the medical image may be generated by any known medical imaging device or system. The medical imaging device or systems may include but are not limited to x-ray, MRI, UT, PET, CT, SPET, mammography, and scintigraphy (such as scintillation cameras) device or system.

The identification information may include at least one of an identifier for a recording device that records the medical image, an identifier for a medical imaging device or system that generates the medical image, acquisition time, image information, image practitioner information, or patient information. The identification information may also include additional information. In some embodiments, the identification information may be included in a DICOM object. In some embodiments, the recording device may be any one or more of an imaging plate, an imaging film, an imaging cassette (e.g., an x-ray cassette), computer-readable storage medium, or any known recording device on which a medical image may be initially recorded. The image information may include attributes of the medical image (e.g., pixel data). The acquisition time may be at least one of date or time at which the medical image was generated. The acquisition time may be in the form of a timestamp.

In some embodiments, the patient image may include identification information. In some embodiments, the medical image may optionally and/or additionally include identification information. The identification information for the patient image and the medical image may be the same or different. The identification information for the patient image and the medical image, respectively, may include the same or different pieces of identification information.

As used herein, a practitioner or an image practitioner may be a user of the system, for example, a physician, radiologist, technologist or technician.

As used herein, a medical facility may be any healthcare institution providing patient treatment, for example, a hospital.

As used herein, a patient may be a human or any animal subject.

As used herein, a generated image series may include at least two images, a patient image and the medical image. In some embodiments, the patient image and the medical image may be of the patient at the same point of care time. The image series may be configured so that the patient image is displayed adjacent to the medical image. In some embodiments, the image series may be an image set.

As used herein, a modality work list or work list may include information associated with a radiology order. In some embodiments, the work list may include radiology order and the study and patient information associated with that order. In some embodiments, the work list may include a plurality of radiology orders associated with the medical imaging device. In some embodiments, the work list may be obtained from a hospital information system or server.

As used herein, an electronic medical record or medical record (also referred to as "EMR") may be a computerized medical record for a patient that may be stored in a hospital information system or server, such as an electronic medical record system.

As used herein, facial recognition algorithm(s) may be any known algorithm, such as geometric or photometric algorithms. The algorithms may include but are not limited to Principal Component, Linear Discriminate Analysis, Elastic Bunch Graph Matching, Hidden Markov model, and the neuronal motivated dynamic link matching.

Image Series Generation Methods

The methods of the disclosure are not limited to the steps and the sequence of the steps described herein. The steps may be individually modified or omitted, as well as additional steps may be added.

Unless stated otherwise as apparent from the following discussion, it will be appreciated that terms such as "receiving," "combining," "reconstructing," "generating," "determining," "obtaining," "processing," "computing," "selecting," "comparing," "associating," "confirming," "converting," "transmitting," "adding," "identifying," "reading," "reconstructing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

FIG. 1 illustrates a method according to embodiments to generate an image series that may include a patient image and a medical image. In some embodiments, a method 100 according to embodiments may include a step 110 for receiving at least one patient image of a patient.

In some embodiments, the method 100 may further include step 120 of receiving identification information. In some embodiments, the identification information may include at least one of an identifier for a recording device that records a medical image, an identifier for a medical imaging device or system that produces the medical image, image information, acquisition time, and patient information.

In some embodiments, the identification information may be received separately from the image of the patient. In some embodiments, the identification information may be included with the image of the patient. In some embodiments, the identification information may be included within a DICOM object. In some embodiments, the identification information may be automatically added to the patient image.

Figure 2:
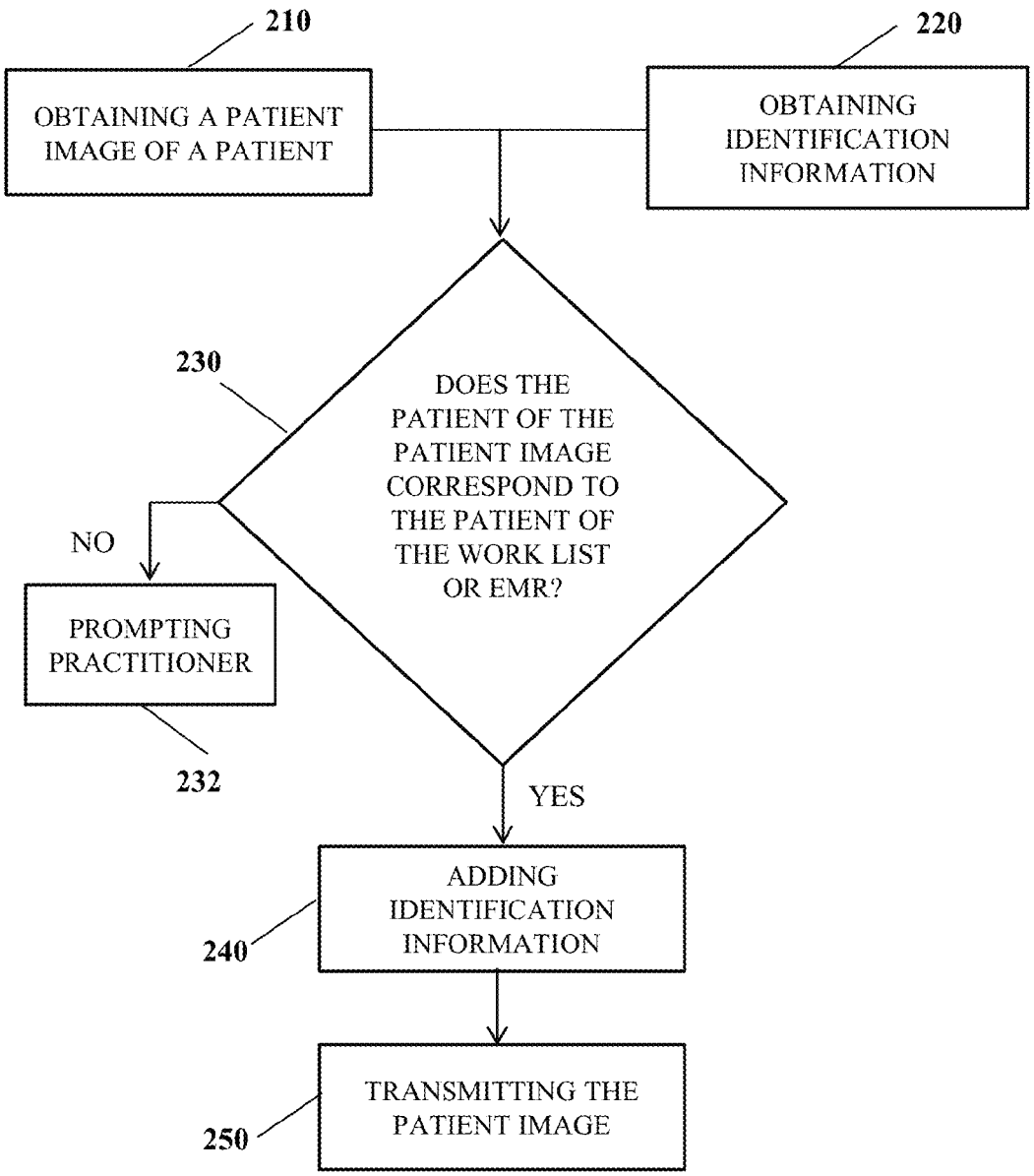
FIG. 2 illustrates a method according to embodiments for obtaining a patient image of a patient.

FIG. 2 shows a method of obtaining identification information and a patient image according to some embodiments. In some embodiments, the method 200 may include a step 210 of obtaining a patient image of a patient. In some embodiments, the step 210 may occur simultaneously, nearly simultaneously, or sequentially, as when a medical image is obtained. The step 210 may automatically be performed when the trigger for acquisition of the medical image is activated.

In some embodiments, the method 200 may further include a step 220 of determining the identification information. In other embodiments, the step 220 may be omitted. The presence and/or modification of the step 220 may depend on the type of medical image recording device and/or configuration of the medical imaging device or system. In some embodiments, the identification information may be obtained by the medical imaging device or other device configured to generate identification information, e.g., DICOM header information. The identification information may be automatically or manually obtained. In some embodiments, the step 220 may occur simultaneously, substantially at the same time, or sequentially with the acquisition of the medical image.

Figure 9:
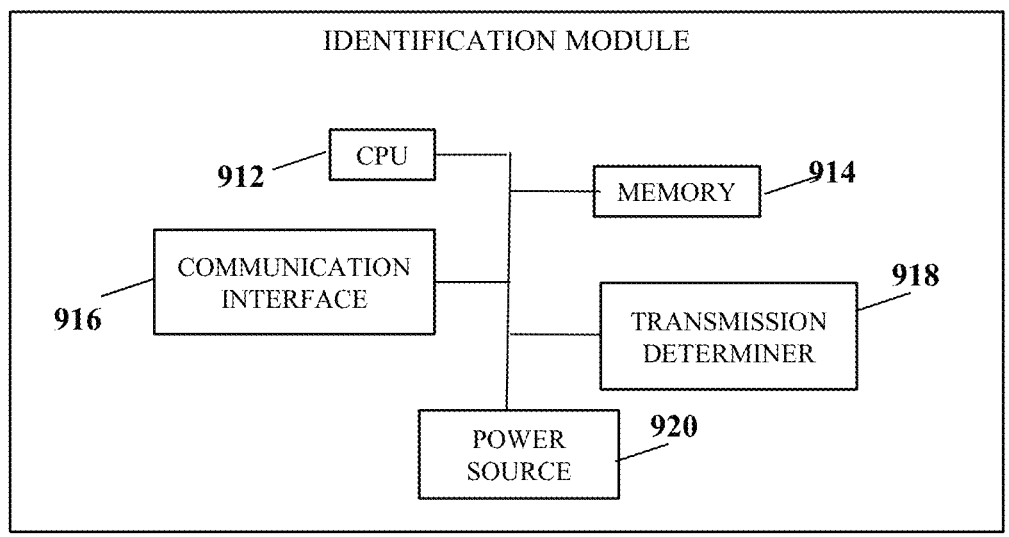
FIG. 9 shows an example of an identification module according to embodiments.

In some embodiments, the identification information may be obtained by reading or receiving data from an electronic tag, label and/or module. In some embodiments, the identification information may be obtained from an identification module. An example of an identification module is shown in FIG. 9. In some embodiments, the identification information may be obtained by a radiofrequency identification (RFID) or barcode reader configured to obtain or read the identification information from a barcode or a RFID tag associated with the image recording device, such as a radiological cassette, or the patient's identification, such as a hospital wrist band. In some embodiments, the RFID reader may be a high-frequency reader that can be configured to automatically read the identification information. In other embodiments, the identification information may be obtained by a radiofrequency (RF) receiver that can be configured to receive or read information from an identification module provided on a radiographic cassette. In some embodiments, the identification information may be obtained according to a method 190 shown in FIG. 1B.

Figure 1B:
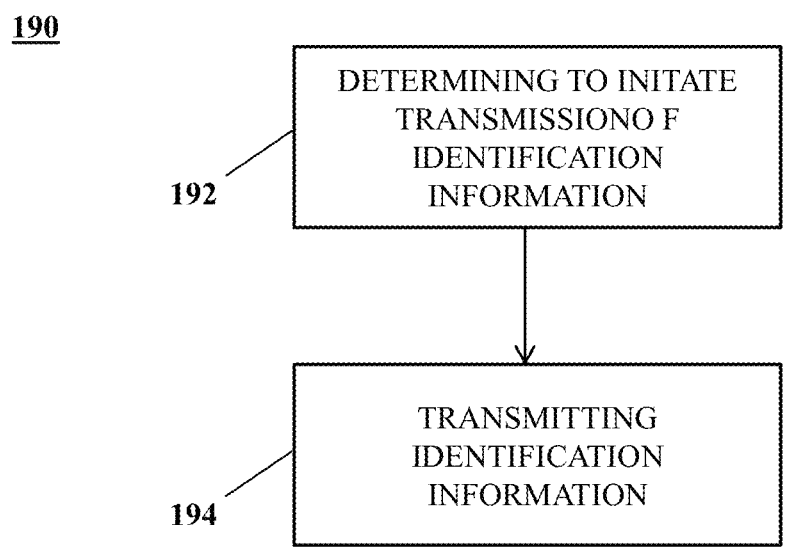
FIG. 1B illustrates a method according to embodiments for determining identification information associated with a radiological cassette.

FIG. 1B shows a method of obtaining identification information using an identification module according to embodiments. In some embodiments, the method 190 may include a step 192 of determining to initiate transmission of identification information. The determining may include detecting imaging of a patient, for example, by detecting light converted from the medical imaging (e.g., radiation (e.g., x-ray) converted to light). The method 190 may further include a step of causing the transmission of identification information. In some embodiments, the identification information may be stored on the identification module.

In some embodiments, the method 200 may optionally include a step 230 of confirming that the patient of the patient image corresponds to the patient associated with the work order (provided on the modality work list), patient information, and/or with the medical record. In some embodiments, the step 230 may occur before the processing of the patient image, such as adding identification information. In some embodiments, the step 230 may occur before the medical image is obtained. In some embodiments, the processing of the patient image and/or the obtaining of the medical image may be performed only after the patient is confirmed. In some embodiments, the step 230 may be performed automatically or manually. In other embodiments, the method may omit the step.

In some embodiments, the confirming step 230 may include comparing the patient image to another patient image or another reference patient image to determine whether the patient of the patient image is the same as the patient associated with the work order/list, electronic medical record and/or patient information. In some embodiments, the comparing may be based on another patient image or reference patient image of the patient associated with associated with the work order/list, electronic medical record and/or patient information.

In some embodiments, the comparing may include comparing a physical characteristic of the patient of the patient image with a physical characteristic of the patient of the other patient image or reference patient image associated with the medical record or work order/list. In some embodiments, the comparing may include extracting the physical characteristic of the patient of the patient image and the physical characteristic the patient of the other patient image or reference patient image. In other embodiments, the physical characteristic may include a physical feature, a facial feature, or a landmark (e.g., anatomic or physiologic) of the patient. In some embodiments, the comparing may be performed automatically, for example, by facial recognition software, or manually. In some embodiments, the patient of the patient image and the patient of the medical image may be compared using facial recognition algorithms In some embodiments, based on the comparing, the method may further include a step 232 of transmitting a prompt indicating a possibility that the patient of the patient image may not correspond to the patient of the medical image. In some embodiments, the prompt may be at least one of a visual alarm and an audible alarm.

In some embodiments, the method may further include a step 240 of adding the identification information to the patient image. The step 240 may occur automatically or manually. In some embodiments, the method 200 may further include converting the patient image to a DICOM format before the step 250 of transmitting the patient image and identification information. In other embodiments, the patient image and identification information may be transmitted without converting the image of the patient. In some embodiments, the patient image may be transmitted to a module provided on the hospital information system, e.g., an electronic medical record system, HIS, RIS and PACS. In other embodiments, the patient image may be transmitted to an image series integration device. In other embodiments, the patient image may be transmitted to a medical imaging device.

According to some embodiments, after the patient image and the identification information are received, the method 100 may further include a step 130 of receiving at least one medical image of a patient. In some embodiments, any number of medical images may be received in step 130. In some embodiments, one medical image may be received. In other embodiments, a plurality of medical images may be received. In some embodiments, each medical image may be an imaging study.

In some embodiments, at least one medical image may be received or obtained from a storage system, such as PACS (picture archiving and communication system). In some embodiments, the medical image may include identification information. The medical image may be in a DICOM format and the identification information for the medical image may be included in the DICOM header.

In some embodiments, the step 130 of receiving the medical image(s) may be based on the identification information received for the patient image. In some embodiments, the receiving of the medical image(s) may be based on one piece of information included in the identification information received. In other embodiments, the medical image(s) received may be based on more than one piece of information included in the identification information received. In further embodiments, the receiving of the medical image(s) may also be based on other information.

For example, in some embodiments, the medical images received may be based on an identifier of the medical imaging device. In other embodiments, the medical images received may be based on acquisition time. In some embodiments, any medical image having an acquisition time that falls within a period of time may be obtained and/or received. The period of time may be predetermined or selected. The period of time may be specific (range of) hours, day(s), or week(s). For example, the medical image(s) obtained and/or received from the storage may be those that fall within a specific twenty-four hour period.

Next, according to some embodiments, the method 100 may further include a step 140 of associating the medical image and the patient image. The step 140 of associating may be based on any or all pieces of the identification information. In some embodiments, the associating may be based on one piece of identification information. In other embodiments, the associating may be based on more than one piece of identification information, for example, acquisition time and the identification information. In further embodiments, the associating may be based on the patient image, such as physical features of the patient.

Figure 3:
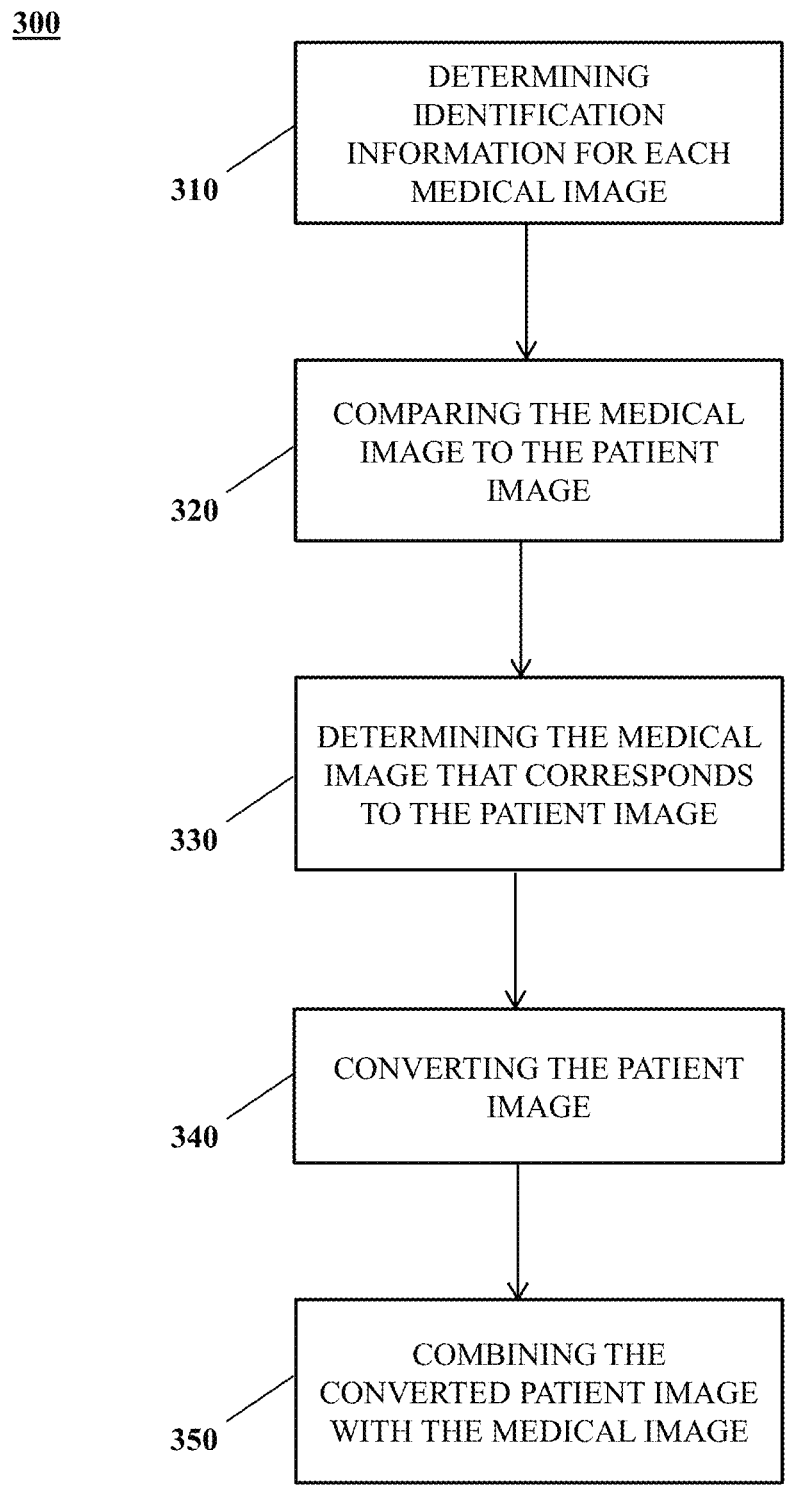
FIG. 3 illustrates a method according to embodiments for associating a patient image with a medical image.

FIG. 3 shows steps of associating according to some embodiments. In some embodiments, an associating step 300 may include a step 310 of obtaining identification information provided with each medical image received. In some embodiments, if the medical image is in DICOM format, the identification information may be provided in the DICOM header. In some embodiments, one piece of the identification information may be obtained. In other embodiments, more than one piece of the identification information may be obtained.

In some embodiments, the associating step 300 may include a step 320 of comparing the received medical image(s) to the image of the patient. In some embodiments, one or more pieces of the identification information for the received medical image(s) may be compared to the respective one or more pieces of the identification information received for the patient image. In some embodiments, the patient of the medical image may be compared to the patient of the patient image.

By providing additional criteria for receiving and/or associating the medical image(s), the potential ambiguity resulting from medical images for different patients that have the same piece(s) of identification information, such as the same recording device identifier, can be addressed. For example, there is a possibility that recording devices, such as x-ray cassettes, are reused and thus there is a possibility that a same recording device identifier may be used in imaging studies involving two different patients.

Figure 4:
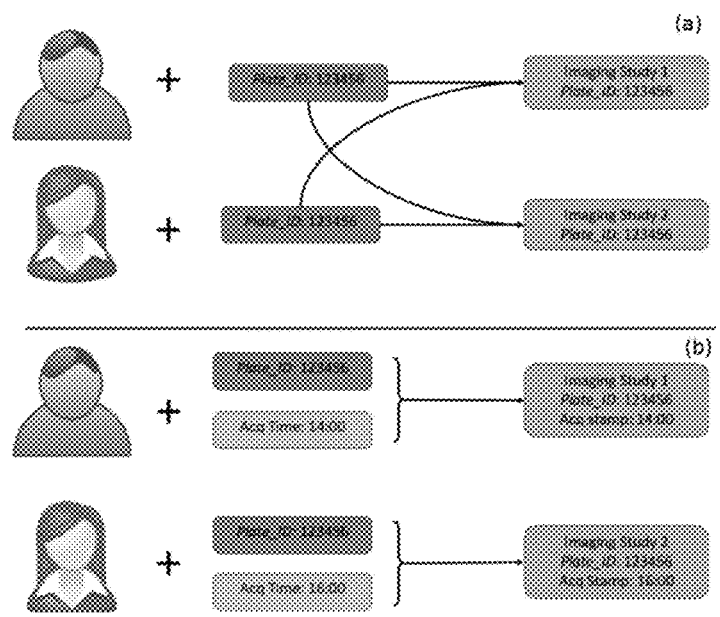
FIG. 4(a) shows an example of an ambiguous relationship between two different patients with same recording device identifier.
FIG. 4(b) shows an example of a proper combination of image of the patient and medical image (imaging study) based on the identifier for the recording device and the acquisition time.

FIG. 4(*a*) illustrates an example of an ambiguous relationship between two different patients with same recording device identifier. FIG. 4(*b*) illustrates an example of a proper combination of image of the patient and medical image (imaging study) based on the identifier for the recording device and the acquisition time.

In some embodiments, the associating step 300 may include a step 330 of determining the medical image that corresponds to the patient image. In some embodiments, the step 330 may include determining the medical image that has the piece(s) of identification information that correspond to the respective piece(s) of identification information of the patient image. In some embodiments, the pieces of identification information for the medical image and the patient image may be the same. In some embodiments, the piece(s) used in the comparing step 320 may be the same used in the determining step 330. In other embodiments, the step 330 may be based on additional pieces of identification information. In some embodiments, the step 330 may be based on the patients of the patient image and the medical image.

In some embodiments, the associating step 300 may further include converting the patient image to another format. The converted format may be the same format as the medical image. In some embodiments, the patient image may be converted to a DICOM format. In some embodiments, the patient image may have been received in the same format as the medical image, such as the DICOM format.

Next, the patient image may be combined with the medical image in a step 350 so that the patient image and medical image are associated.

Figure 5:
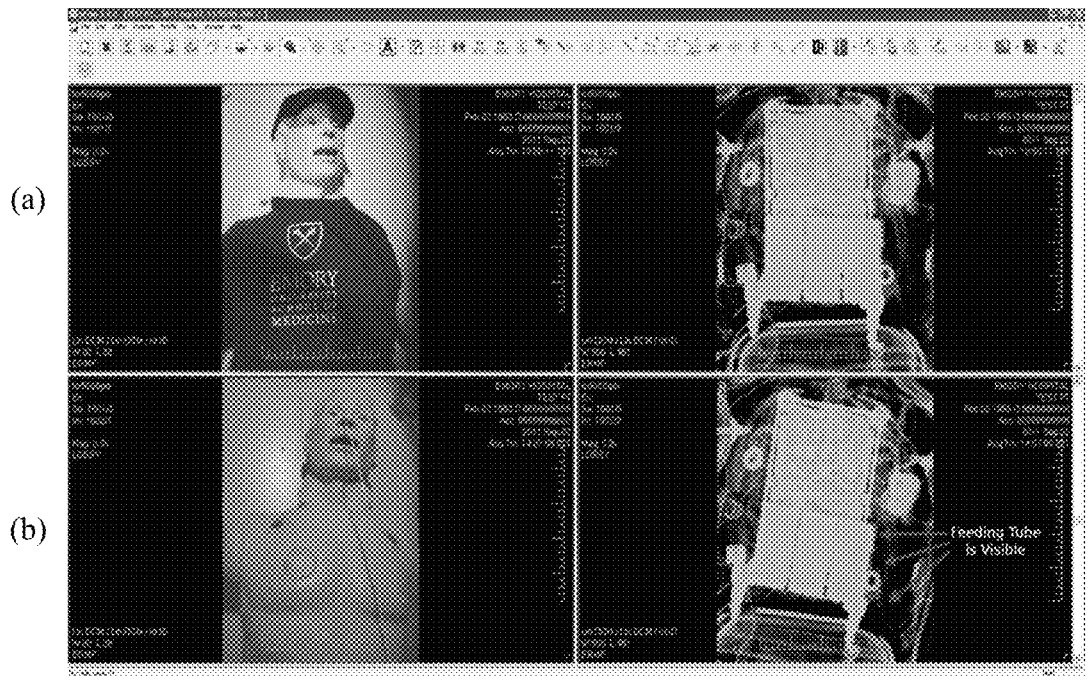
FIGS. 5(a) and 5(b) show an example of a generated image series and a comparison series.

After the patient image and the medical image are associated, the method 100 may further include generating a new image series that includes the patient image and the medical image in step 150. An example of the generated image series and a comparison series are illustrated in FIGS. 5(*a*) and (*b*).

In some embodiments, the method 100 may further include a step 160 of confirming that the image series is properly associated with at least one of a medical record, patient information, or work order before the image series is transmitted to a peripheral device or stored. In some embodiments, the step 160 may confirm that the patient of the patient image corresponds to the patient associated with the work order (provided on the modality work list) and/or with the medical record. In some embodiments, the step 160 may occur before or after the image series is generated. In some embodiments, the step 160 may be performed automatically or manually. In other embodiments, the method may omit the step.

In some embodiments, the confirming step 160 may include comparing the patient of the image series to another patient image or another reference patient image to determine whether the patient of the patient image is the same as the patient associated with the work order/list, electronic medical record and/or patient information. In some embodiments, the comparing may be based on another image series, another medical image, another patient image, and/or a patient image of the patient associated with the work order/list, electronic medical record and/or patient information. In some embodiments, the comparing may be based on another image series that includes the patient image and the medical image associated with the medical record, for example, as shown in FIGS. 5(a) and 5(b).

In some embodiments, the comparing may include comparing a physical characteristic of the patient of the patient image with a physical characteristic of the patient of the medical image. In some embodiments, the comparing may include comparing a physical characteristic of the patient of the patient image with a physical characteristic of the patient of the other patient image or reference patient image associated with the medical record or work order/list. In some embodiments, the comparing may include extracting the physical characteristic of the patient of the patient image and the physical characteristic the patient of the other patient image or reference patient image. In some embodiments, the comparing may include extracting the physical characteristic of the patient of the patient image and the physical characteristic of the patient of the medical image. In other embodiments, the physical characteristic may include a physical feature, a facial feature, or a landmark (e.g., anatomic or physiologic) of the patient. In some embodiments, the comparing may be performed automatically, for example, by facial recognition software, or manually. In some embodiments, the patient of the patient image and the patient of the medical image may be compared using facial recognition algorithms.

In some embodiments, based on the comparing, the method may further include a step 170 of transmitting a prompt indicating a possibility that the patient of the patient image may not correspond to the patient of the medical image. In some embodiments, the prompt may be at least one of a visual alarm and an audible alarm.

In further embodiments, after a prompt is transmitted, the practitioner may be required to view the generated image series and another patient image, image series and/or reference patient image to confirm whether the patient of the image series is associated with the correct medical record, work order/list and/or patient information. The generated image series may be displayed so that the practitioner may be able to view the generated image series.

In some embodiments, the practitioner may manually compare the patient image of the generated series and another patient image, image series and/or reference patient image to confirm whether the patient of the image series is associated with the correct medical record, work order/list and/or patient information to confirm that the series is properly associated with the correct medical record, work order/list and/or patient information. The confirming step may include displaying the generated series. The practitioner may confirm that the generated image series is properly associated after viewing and visually comparing the images.

In some embodiments, the method may further include, alternatively or additionally, repeating the method until a proper image series is determined. In some embodiments, the steps of receiving medical images and the proceeding steps may be repeated until a proper image series is determined. In other embodiments, the steps of associating and the proceeding steps may be repeated until a proper image series is determined.

In some embodiments, after the image series is generated and/or confirmed, the method may further include steps of 182, 184 and 186 of displaying, storing and/or printing the image series. In some embodiments, the image series may be displayed, stored, and/or printed. In some embodiments, the image series may be transmitted to another server or storage device for the printing, displaying and/or storing the image series. In some embodiments, the displaying may include displaying the generated image series for interpretation. In some embodiments, the image series may be transmitted to another storage system provided on the hospital information system, such as PACS. The series may be associated with the medical record.

Figure 6:
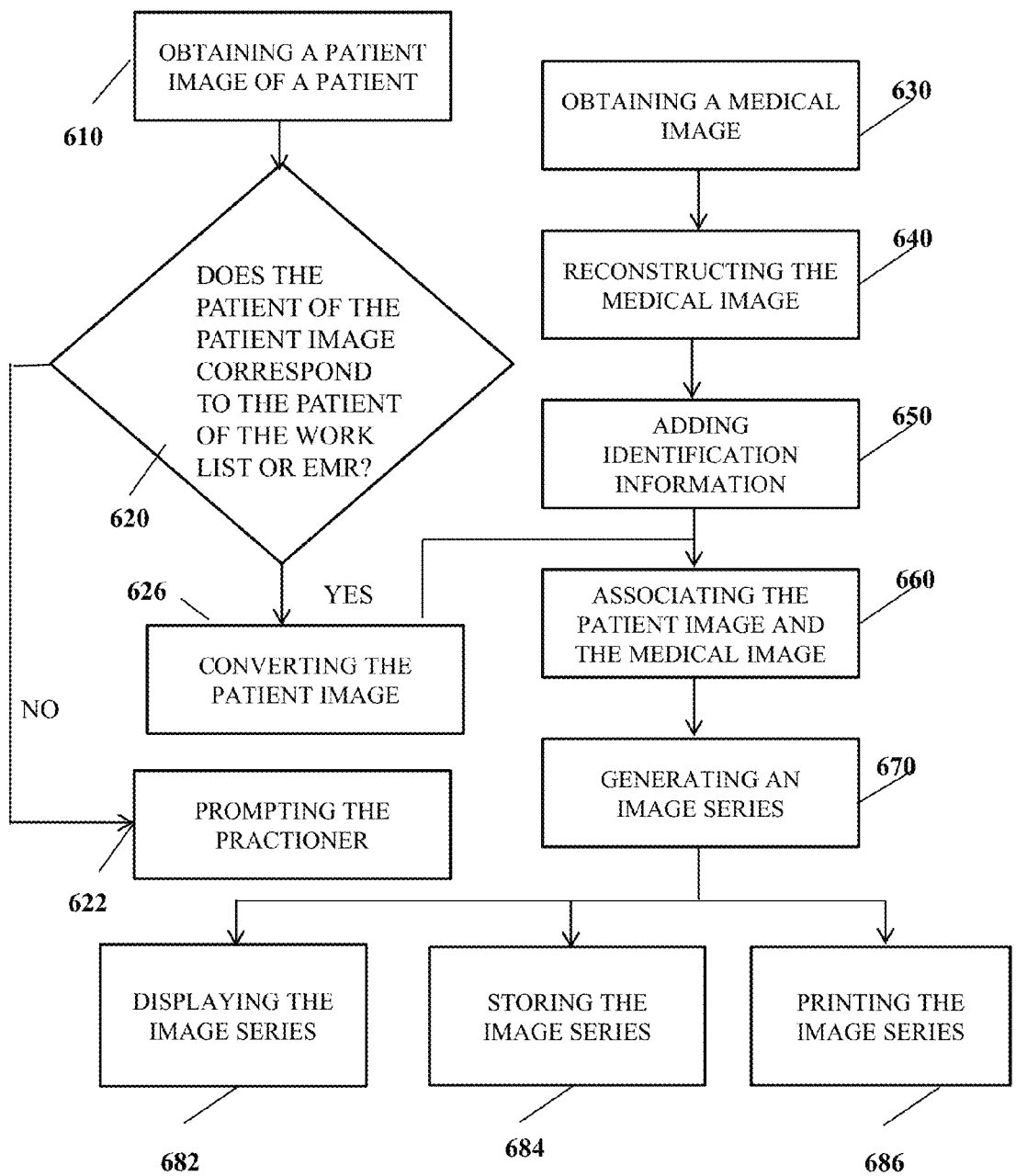
FIG. 6 illustrates a method according to other embodiments for generating an image series.

FIG. 6 illustrates a method according to alternative embodiments to generate an image series that may include a patient image and corresponding medical image. In some embodiments, the identification information and the image series may be generated by the medical imaging device.

In some embodiments, method 600 may include a step 610 of obtaining a patient image of a patient. This step may occur simultaneously, nearly simultaneously, or sequentially, as when a medical image of the patient is obtained (step 630). The step 610 may automatically be performed when the trigger for acquisition of the medical image is activated. The trigger may be a manual, software driven and/or hardware driven.

In some embodiments, the method 600 may optionally include a step 620 of confirming that the patient of the patient image corresponds to the patient associated with the work order (provided on the modality work list), patient information and/or with the medical record. In some embodiments, the step 620 may occur after the processing of the patient image (step 626). In some embodiments, the step 620 may occur before the medical image is obtained (step 630). In some embodiments, the processing of the patient image and/or the obtaining of the medical image may be performed only after the patient is confirmed. In some embodiments, the step 620 may be performed automatically or manually. In other embodiments, the method may omit the step.

In some embodiments, the confirming step 620 may include comparing the patient image to another patient image or another reference patient image to determine whether the patient of the patient image is the same as the patient associated with the work order/list, electronic medical record and/or patient information. In some embodiments, the comparing may be based on another patient image or reference patient image of the patient associated with associated with the work order/list, electronic medical record and/or patient information.

In some embodiments, the comparing may include comparing a physical characteristic of the patient of the patient image with a physical characteristic of the patient of the other patient image or reference patient image associated with the medical record or work order/list. In some embodiments, the comparing may include extracting the physical characteristic of the patient of the patient image and the physical characteristic the patient of the other patient image or reference patient image. In other embodiments, the physical characteristic may include a physical feature, a facial feature, or a landmark (e.g., anatomic or physiologic) of the patient. In some embodiments, the comparing may be performed automatically, for example, by facial recognition software, or manually. In some embodiments, the patient of the patient image and the patient of the medical image may be compared using facial recognition algorithms.

In some embodiments, based on the comparing, the method may further include a step 622 of transmitting a prompt indicating a possibility that the patient of the patient image may not correspond to the patient of the medical image. In some embodiments, the prompt may be at least one of a visual alarm and an audible alarm. In some embodiments, the step 622 may further include preventing the obtaining of a medical image (step 630).

Next, the method may further include a step 626 of converting the patient image. In some embodiments, the image of the patient may be converted to another format so that it may be processed by the medical imaging device. The converted format may be the same format as the medical image. In some embodiments, the image of the patient may be converted to a DICOM format. In some embodiments, the image of the patient may have been received in the same format as the medical image, such as the DICOM format.

The method 600 may include a step 630 of obtaining a medical image. The step 630 may be according to the medical image device. Next, the method may include a step 640 of reconstructing the medical image. The step 640 may depend on the type of medical device and may be omitted. The step 640 may be according to any known reconstruction methods. Reconstruction methods may include but are not limited to Fourier transform.

The method 600 may further include a step of 650 of adding identification information. The step 650 of adding the identification information may include generating the identification information. The identification information may be in a form of a DICOM header.

The method 600 may further include a step 660 of associating the patient image and the medical image. The step 660 may include combining the medical image and the patient image.

The method 600 may further include a step 670 of generating an image series.

In some embodiments, after the image series is generated and/or confirmed, the method may further include steps of 682, 684 and 686 of displaying, storing and/or printing the image series. In some embodiments, the image series may be displayed, printed, or stored. In some embodiments, the image series may be transmitted to another server or storage device for the printing, displaying and/or storing the image series. In some embodiments, the displaying may include displaying the generated image series for interpretation. In some embodiments, the image series may be transmitted to another storage system provided on the hospital information systems, such as PACS. The series may be associated with the medical record.

In some embodiments, the steps of the methods may be performed over a network that is wired, wireless, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network, such as ZigBee.

System Implementation

Figure 7:
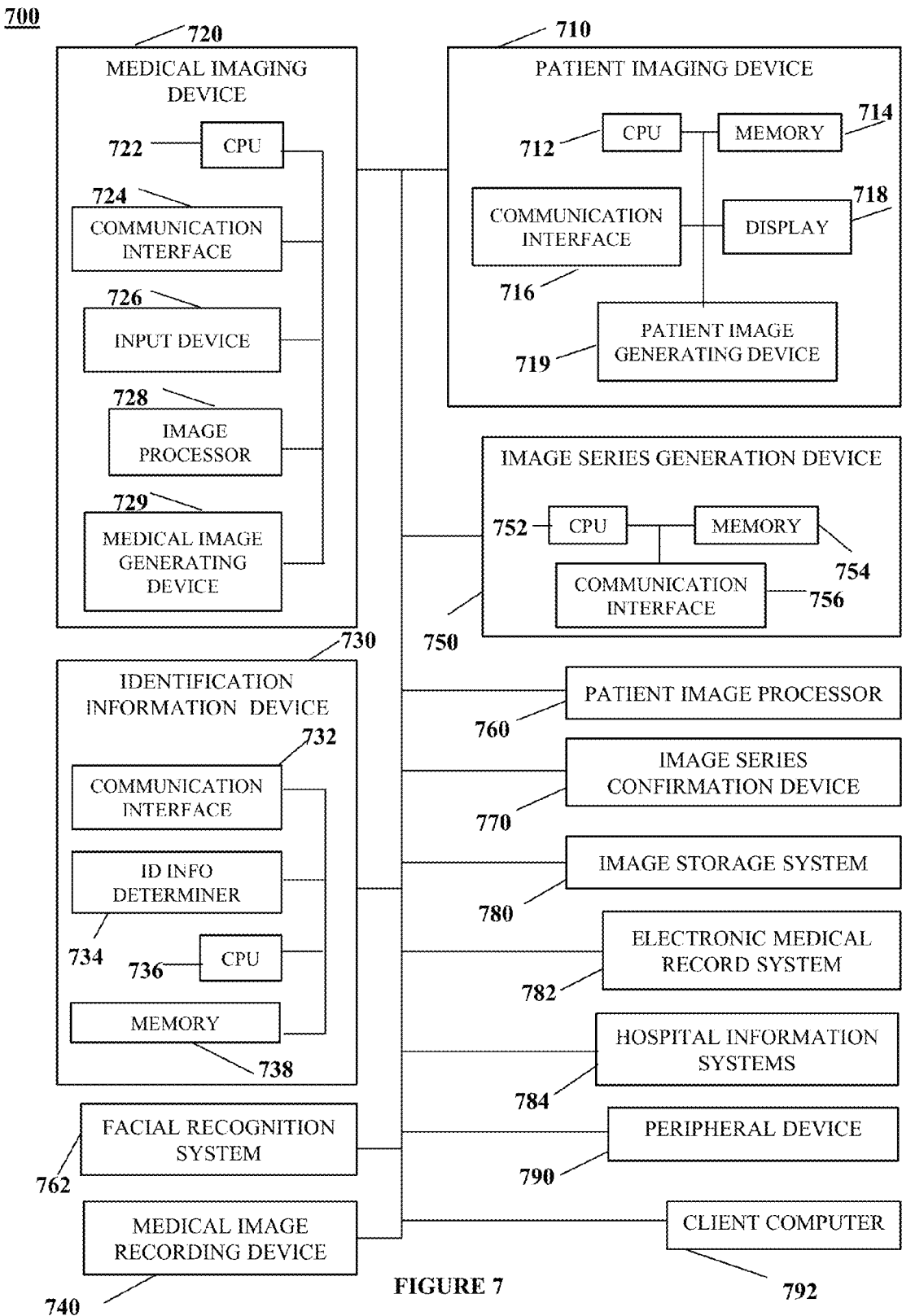
FIG. 7 shows an example of a medical facility network system that may be used to generate an image series according to embodiments.

FIG. 7 shows an example of a medical facility network system that may be used to generate an image series according to embodiments. The system 700 may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network, such as ZigBee.

Although the modules of the system are shown as being directly connected, the modules may be indirectly connected to one or more of the other modules of the system. In some embodiments, a module may be only directly connected to one or more of the other modules of the system.

It is also to be understood that the system may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the system may be time synchronized. In further embodiments, the system may be time synchronized with other systems, such as those systems that may be on the medical facility network.

As shown in FIG. 7, a system 700 may include a patient imaging system 710. The patient imaging system 710 may be configured to obtain still or video digital photographs. In some embodiments, the patient imaging device may be a separate, peripheral device. In other embodiments, the patient imaging system may be integrated with another system or device. In some embodiments, the patient imaging system 710 may be integrated with a medical imaging device or system. In some embodiments, the patient imaging system 710 may be any digital device having imaging capabilities. The patient imaging system 710 may include but is not limited to a mobile computing device, such as a smart phone or tablet device.

In some embodiments, the patient imaging system 710 may include CPU 712. The CPU 712 may be one or more of any known central processing unit, including but not limited to a processor, a microprocessor, and/or microcontroller. The CPU 712 may be configured to control the capturing of the image(s) of the patient. The CPU 712 may be coupled directly or indirectly to memory elements, such as memory 714. The memory 714 may include random access memory (RAM), read only memory (ROM), disk drive, tape drive, etc., or a combinations thereof. The memory 712 may also include a frame buffer for storing image data arrays.

The patient imaging system 710 may further include a communication interface 716 configured to conduct receiving and transmitting of data between the patient imaging system 710 and other modules on the system and/or network. The communication interface 716 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the medical facility network.

In some embodiments, the patient imaging system 710 may further include display 718. The display 718 may be any known display, such as a CRT (Cathode Ray Tube), a LCD (Liquid Crystal Display) or OLED (Organic Light-emitting Diode).

The patient image generating device 719 may be a device configured to take or obtain still or dynamic images. The patient image generating device 719 may be a charge-coupled device or a complementary metal oxide semiconductor (CMOS) camera.

In some embodiments, the system 700 may further include a patient image processor 760. The patient image processor 760 may be configured to process the patient image for an image integration device 750. In some embodiments, the patient image processor 760 may be configured to convert the patient image into another format. For example, the patient image processor 760 may be configured to convert a JPEG into a DICOM standard format. In some embodiments, the patient image processor 760 may be a separate device. In other embodiments, the patient image processor may be a part of other modules, such as the patient imaging system 710, the medical imaging device or system 720, and/or the image series generation device 750.

In some embodiments, the system 700 may further include a medical imaging device or system 720. In some embodiments, the patient imaging system 710 may be integrated with the medical imaging device 720. In other embodiments, the patient imaging system 710 may be a separate, peripheral device.

In some embodiments, the medical imaging device 720 may be any known medical imaging system. In some embodiments, the medical imaging device 720 may be a stationary system. In other embodiments, the medical imaging system may be a mobile system. The medical imaging device or system 720 may include any known modality. The medical imaging device 720 may include but is not limited to radiography, Computed Tomography (CT), ultrasound (US), magnetic resonance imaging (MRI), scintigraphy, mammography, single-photon emission computed tomography (SPET) and positron-emission-tomography (PET) modalities. Examples of the medical imaging device or system may include but are not limited to x-ray, MRI, UT, PET, CT, SPET, mammography, or scintigraphy (such as scintillation cameras) devices or systems. Various combinations of such devices are also possible, for example, PET-CT or PET-MRI devices.

In some embodiments, the medical imaging device 720 may include a computer system to carry out the image processing. The computer system may further be used to control the operation of the system or a separate system may be included.

The medical imaging device 720 may include a CPU 722. The CPU 722 may be one or more of any known central processing unit, including but not limited to a processor, a microprocessor, and/or microcontroller. The CPU 722 may be coupled directly or indirectly to memory elements, such random access memory (RAM), read only memory (ROM), disk drive, tape drive, etc., or a combinations thereof. The memory may also include a frame buffer for storing image data arrays.

The medical imaging device 720 may further include a communication interface 724 configured to conduct receiving and transmitting of data between the medical imaging system 720 and other modules on the system and/or network. The communication interface 724 may be a wired and/or wireless interface, a switched circuit wireless interface, a network of data processing devices, such as LAN, WAN, the internet, or combination thereof. The communication interface 724 may be configured to execute various communication protocols, such as Bluetooth, wireless, and Ethernet, in order to establish and maintain communication with at least another module on the medical facility network.

In some embodiments, the medical imaging device 720 may include an input device 726 configured to control the generation of the medical images, display of medical images on a display, and/or printing of the images by a printer interface. The input device 726 may include a mouse, joystick, keyboard, track ball, touch activated screen, light wand, voice control, or any similar or equivalent input device, and may be used for interactive geometry prescription. In some embodiments, the input device 726 may be configured to also control the patient imaging device 710. The input device 726 may be configured to control the generation of the patient images, display of patient images on a display, and/or printing the patient images by a printer interface. In some embodiments, the input device 726 may be configured to control the medical imaging device 720 and the patient imaging device 710 to simultaneously obtain the medical image and the patient image, respectively, simultaneously, substantially the same time, or sequentially.

In some embodiments, the medical imaging device 720 may further include an image processor 728. The image processor 728 may be one or more of any known central processing unit, including but not limited to a processor, or a microprocessor. In some embodiments, the image processor 728 may be configured to process the medical image data, for example, reconstructing the image data. In other embodiments, the image processor 728 may be replaced by image processing functionality on the CPU 722.

In some embodiments, the medical imaging device 720 may further include a medical image generating device 729 configured to generate a medical image. The medical image generating device 729 may depend on the type of medical imaging technique. For example, for a MRI technique, the medical image generating device 729 may be configured to generate and detect the magnetic field to generate a medical image.

In some embodiments, the medical imaging device 720 may store the generated medical image(s) on a medical image recording device 740. The medical image recording device 740 may be any one or more of an imaging plate, an imaging film, a computer-readable storage medium, or any known recording device on which a medical image may be initially recorded. In some embodiments, the medical image recording device 740 may be a memory component integral with the medical imaging system. In other embodiments, the medical image recording device 740 may be physical storage medium, such as a radiological or x-ray cassette.

In some embodiments, the system 700 may further include an identification information device 730 (also referred to as "identification information input device") configured to determine identification information to add to the patient image and/or medical image. The identification information device 730 may be a separate, peripheral device that may be in communication with the patient imaging system and/or medical imaging system. In other embodiments, the identification information determination device 730 may be integrated with the patient imaging system, medical imaging system, the integration server, or a combination thereof.

In some embodiments, the system 700 may include more than one identification information device 730. In some embodiments, each of the medical imaging system 720 and the patient imaging system 710 may include an identification information device 730. The identification information device of each module may be the same or may be different.

In some embodiments, the identification information device 730 may be configured to automatically generate the identification information. In some embodiments, the identification information device 730 may be configured to generate a DICOM header including the identification information. In other embodiments, the identification information device 730 may be configured to read and/or receive identification information.

In some embodiments, the identification information device 730 may include a communication interface 732 configured to conduct receiving and transmitting of data between identification information device 730 and other modules, e.g., modules on the system and/or network, an identification information module, or a combination thereof. The communication interface 732 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the medical facility network. In some embodiments, the identification information determination device 730 may further include an identification information determiner 734 (also referred to as "identification information generator"). The identification information determiner 734 may be configured to determine and/or obtain identification information. In other embodiments, the identification information determiner may be configured to read or receive identification information. In some embodiments, the identification information determiner 734 may be an RFID or bar code reader. In some embodiments, the RFID reader may be a high-frequency reader. The identification information determiner 734 may be configured to read information from a barcode label or RFID label provided on a medical image recording device 740, such as an x-ray cassette. In other embodiments, the identification information determiner 734 may be configured to read patient identification information provided on, for example, a medical facility or hospital wristband.

In other embodiments, the identification information determiner 734 may include a RF transceiver configured to receive identification information, for example, from an identification module provided on a radiological cassette. An example of an identification module according to embodiments is shown in FIG. 9. In some embodiments, the identification information determiner 734 may be a part of the communication interface 732.

In some embodiments, the identification information device 730 may further include a CPU 736. The CPU 736 may be one or more of any known central processing unit, including but not limited to a processor, or a microprocessor. The CPU 736 may be configured to control the capturing of the image(s) of the patient. The CPU 736 may be coupled directly or indirectly to memory elements, such as memory 738. The memory 738 may include random access memory (RAM), read only memory (ROM), disk drive, tape drive, etc., or a combinations thereof. The memory 738 may also include a frame buffer for storing image data arrays.

The system 700 may further include an image series generation device 750. The image series generation device 750 may be configured to generate an image series including an image of a patient and a medical image of the patient. In some embodiments, the image series generation device 750 may be configured to obtain medical images from the image storage system 780, for example, based on the identification information on the received patient image. The image series generation device 750 may also be referred to as an "integration server."

In some embodiments, the image series generation device 750 may be a separate device. In other embodiments, the image series generation device 750 may be a part of other modules of the system, for example, the medical imaging system 720.

The image series generation device 750 may include a CPU 752. The CPU 752 may be one or more of any known central processing unit, including but not limited to a processor, a microprocessor, and/or microcontroller. The CPU 752 may be coupled directly or indirectly to a memory 754. The memory 754 may be memory elements, such random access memory (RAM), read only memory (ROM), disk drive, tape drive, etc., or a combinations thereof. The memory may also include a frame buffer for storing image series data arrays.

The image series generation device 750 may further include a communication interface 756 configured to conduct receiving and transmitting of data between the image series generation device 750 and other modules on the system and/or network. The communication interface 756 may be a wired and/or wireless interface, a switched circuit wireless interface, a network of data processing devices, such as LAN, WAN, the internet, or combination thereof. The communication interface 756 may be configured to execute various communication protocols, such as Bluetooth, wireless, and Ethernet, in order to establish and maintain communication with at least another module on the medical facility network.

In some embodiments, the system 700 may further include a facial recognition system 762. The facial recognition system 762 may be configured to compare characteristics of a patient image or medical image to characteristics of another patient image or medical image. In some embodiments, the facial recognition system 762 may be configured to extract the physical characteristic(s) of the patients of the images. In some embodiments, the physical characteristic may include a physical feature, a facial feature, or a landmark (e.g., anatomic or physiologic) of the patient. The facial recognition system 762 may be facial recognition software using known facial recognition algorithms. In some embodiments, the facial recognition system 762 may be a separate device. In other embodiments, the facial recognition system 770 may be a part (e.g., stored on the memory) of other modules, for example, the image series generation device 750, the identification information input device 732, the medical imaging device 720 and/or the patient imaging device 710, and controlled by its respective CPUs.

In some embodiments, the system 700 may further include an image series confirmation device 770. The image series confirmation device 770 may be configured to compare the generated image series to determine whether the image of the patient and the medical image are properly associated. In some embodiments, the image series confirmation device 770 may be a separate device. In other embodiments, the image series confirmation device 770 may be a part of other modules, for example, the image series generation device 750, and controlled by its respective CPUs.

In some embodiments, the system may further include an image storage system 780. The image storage system 780 may be a PACS system.

In some embodiments, the system 700 may further include and/or be connected to other information systems of the medical facility network. For example, the modules of the system 700 may be connected to an electronic medical record system 782 and/or other hospital information systems 784.

The electronic medical record system 782 may be an electronic health record (HER) and/or an electronic medical record (EMR) system. The other hospital information systems 784 may include but are not limited to radiology information system (RIS) and cardiovascular imaging systems (CVIS), practice management system (PMS), and other hospital information systems.

In some embodiments, the system 700 may further include at least one peripheral device 790. The peripheral device 790 may include, but is not limited to, a printer device.

In some embodiments, the system 700 may further include at least one client computer 792. The client computer 792 may be coupled to other client computers or servers. According to some embodiment, the client computer 792 may be configured to access any of the modules provided in the system. The client computer 792 may be a basic computer system. The client computer 792 may include a CPU, a memory, an input device, a display and a printer interface. The client computer may be a mobile handheld computer, such as a tablet device and/or smart phone. The client computer 792 may be configured to obtain and to display the image series for example, for viewing, confirmation and/or interpretation.

FIG. 9 shows an example of an identification information module 900 that may be used to determine identification information according to embodiments. In some embodiments, the information identification module 900 may be fixedly or removably disposed on a medical imaging recording device (e.g., radiological cassette, such as, an x-ray cassette). In other embodiments, the information identification module 900 may be disposed on another entity, such as a wrist band or a platform of the medical imaging device. In some embodiments, the identification information module 900 may include further include a CPU 912. The CPU 912 may be one or more of any known central processing unit, including but not limited to a processor, a microprocessor, and/or microcontroller. The CPU 912 may be a low power embedded processor. The CPU 912 may be configured to control the transmission of identification information, for example, to the integration server. The CPU 912 may be coupled directly or indirectly to memory elements, such as memory 914. The memory 914 may include random access memory (RAM), read only memory (ROM), disk drive, tape drive, etc., or a combinations thereof. The memory 914 may also include a frame buffer for storing image data arrays. The memory 914 may store the identification information.

The information identification module 900 may further include a communication interface 916. The communication interface 916 may be configured to communicate with an integration server, the medical imaging device, patient imaging device, as well as other modules on the hospital network. The communication interface 916 may be configured to transmit the identification information. The communication interface 916 may include an RF transceiver (e.g., a low power RF transceiver) configured to transmit the identification information stored on the memory 914.

In some embodiments, the identification information module 900 may include a transmission determiner 918. The transmission determiner 918 may configured to determine when to initiate transmission of the identification information. In some embodiments, the transmission determiner 918 may include a sensor configured to detect when the imaging of the patient occurs. In some embodiments, the transmission determiner 918 may be configured to detect radiation or an x-ray. In some embodiments, the transmission determiner 918 may include a scintillator bonded to a light sensor (e.g., photo-sensitive diode). The scintillator can be configured to convert x-rays to visible light, which in-turn is converted into a digital output by the light sensor. This may result in the communication interface 916 to wirelessly transmit the identification information stored in the memory 914 when the patient is imaged.

The identification information module 900 may further include a power source 920. The power source 920 may be any battery.

Figure 8:
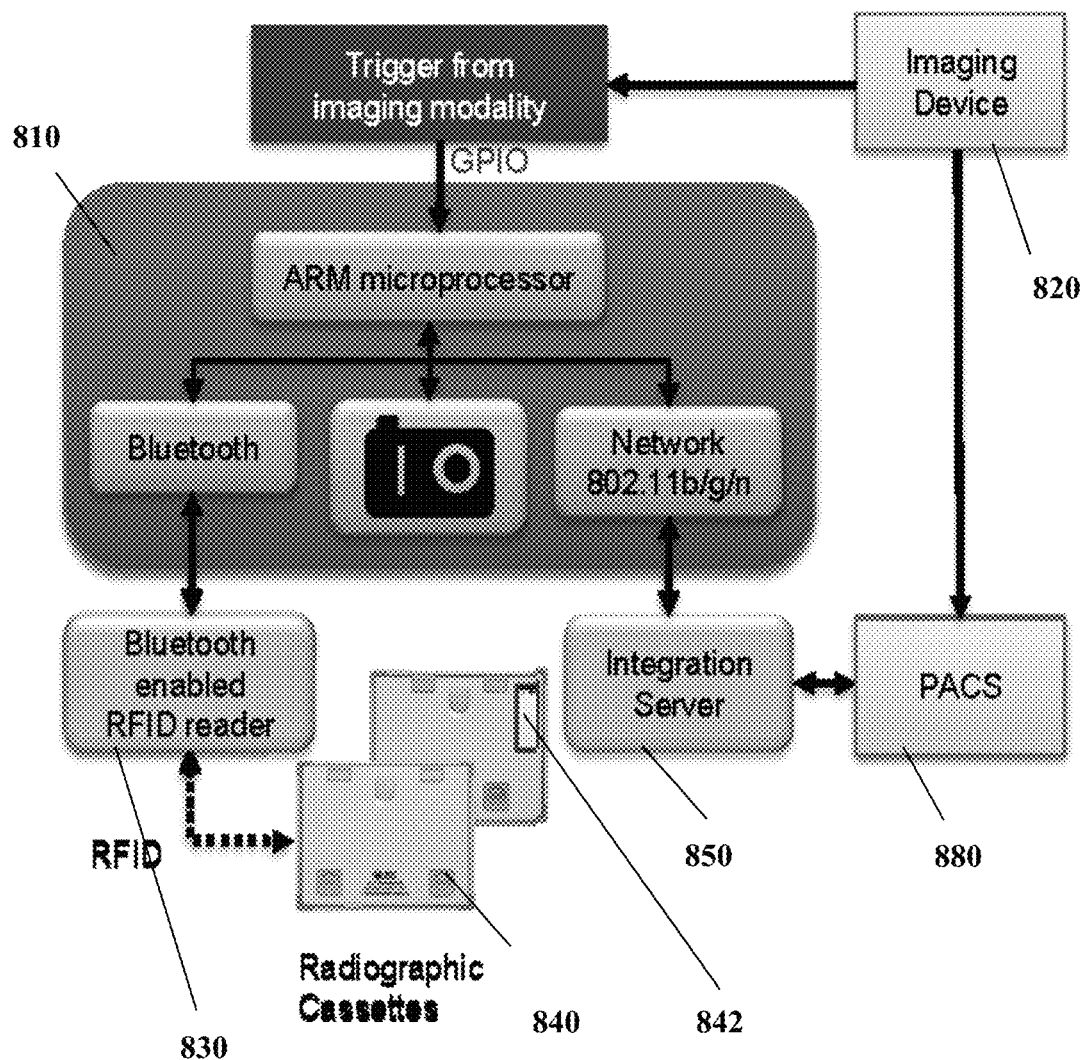
FIG. 8 shows another example of a system according to embodiments.

FIG. 8 illustrates another example of a system according to some embodiments. As shown in FIG. 8, the system 800 may include a patient imaging system 810, a medical imaging system 820, an identification information device 830, a medical image recording device 840, an image series generation device 850, and an image storage system 880. The medical image recording device 840 may include an identification information module 842. The system 800 may be configured so that the patient imaging system 810 and identification information device 830 may be controlled by the imaging device 820. For example, the patient imaging system 810 may be configured to obtain a patient image and the identification information device 830 may be configured to obtain the identification information from the medical image recording devices 840 when the medical imaging device 820 is triggered by the practitioner to acquire the medical image. In some embodiments, the identification information device 830 may be configured to receive the identification information from the identification module 842. This may result in reading of the identification information and the obtaining of the patient image and medical image to occur simultaneously or substantially the same time.

As shown in FIG. 8, the patient imaging system 810 may be an imaging device with communication capabilities. The patient imaging system 810 may have both Bluetooth and wireless communication capabilities configured to communicate with the identification information device 830 and the image series generation device 850, respectively.

The image series generation device (the integration server) 850 may be configured to communicate with the patient imaging system 810 to receive a patient image and the identification information and to communicate with the image storage system (PACS) 880 to receive the medical image of the patient.

In some embodiments, the disclosed methods (e.g., FIGS. 1-3 and 6) may be implemented using software applications that are stored in a memory and executed by a CPU provided on the system. In some embodiments, the disclosed method s may be implanted using software applications that are stored in memories and executed by CPUs distributed across the system. As such, the modules of the system may be a general purpose computer system that becomes a specific purpose computer system when executing the routine of the disclosure. The modules of the system may also include an operating system and micro instruction code. The various processes and functions described herein may either be part of the micro instruction code or part of the application program or routine (or combination thereof) that is executed via the operating system. In addition, various other peripheral devices may be connected to the computer platform such as an additional data storage device, a printing device, and other I/O (input/output) devices.

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures may be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as series forth in the appended claims. For example, elements and/or features of different exemplary embodiments may be combined with each other and/or substituted for each other within the scope of this disclosure and appended claims.

What is claimed is:

1. A computer-implemented method for generating an image series, comprising:
   receiving at least one medical image of a patient acquired by a medical imaging device and recorded onto a recording device;
   receiving identification information associated with the at least one medical image when acquisition of the at least one medical image is detected by an image-activated circuitry,
the identification information including an acquisition time of the at least one medical image and an identifier for the recording device;
   receiving at least one patient image of the patient acquired by a camera and identification information associated with the at least one patient image when the acquisition of the at least one medical image is detected, the identification information including an acquisition time of the patient image and the identifier for the recording device;
   associating the at least one patient image and the at least one medical image based on the identification information; and
   generating an image series that includes the at least one patient image and the at least one medical image.

2. The method according to claim 1, wherein the identification information includes at least one of an identifier for the medical imaging device that acquires the at least one medical image, image information, image practitioner information, or patient information.

3. The method according to claim 1, wherein:
   the identification information is included in a DICOM object; and
   the recording device is a radiological cassette.

4. The method according to claim 1, further comprising:
   receiving a plurality of different medical images based on the identification information for each medical image, wherein the identification information for each medical image includes an acquisition time within a specific time period and an identifier for the recording device on which the each medical image is recorded.

5. The method according to claim 4, further comprising:
   comparing the plurality of different medical images to the at least one patient image;
   receiving the identification information for each of the plurality of medical images; and
   determining one or more medical images of the plurality of different medical images that corresponds to the at least one patient image based on the identifier of the recording device and the acquisition time.

6. The method according to claim 1, further comprising confirming that the image series is properly associated with at least one of a medical record, patient information, or work order.

7. The method according to claim 6, further comprising:
   comparing the patient of the image series to a patient associated with at least one of a medical record, patient information, or work order to determine whether the patient of the image series corresponds to the patient associated with the medical record, patient information, or work order.

8. The method according to claim 7, wherein:
   the comparing includes at least one of comparing the generated image series to another medical image associated with a medical record or comparing the generated image series to another patient image associated with the medical record; and
   the medical record corresponds to at least one piece of the identification information.

9. The method according to claim 8, the comparing may include comparing a physical characteristic of the patient of the at least one patient image to the other patient image.

10. The method according to claim 1, further comprising displaying the at least one patient image and the at least one medical image of the image series, wherein the at least one patient image is adjacent to the at least one medical image.

11. The method according to claim 1, wherein the at least one patient image includes a portion of a body of the patient.

12. The method according to claim 1, further comprising:
    detecting the acquisition of the at least one medical image of the patient.

13. The method according to claim 12, further comprising:
    causing the at least one image of the patient to be acquired by the camera when the acquisition of the at least one medical image is detected.

14. A non-transitory computer-readable storage medium storing instructions for generating an image series, the instructions comprising:
    causing acquisition of at least one medical image of a patient by a medical imaging device and recordation of the at least one medical image onto a recording device;
    causing identification information associated with the at least one medical image to be transmitted when the acquisition of the at least one medical image is detected by an image-activated circuitry, the identification information including an acquisition time of the at least one medical image and an identifier for the recording device;
    receiving at least one patient image of the patient acquired by a camera and identification information associated with the at least one patient image when the acquisition of the at least one medical image is detected, the identification information including an acquisition time of the at least one patient image and the identifier for the recording device;
    associating the at least one patient image and the at least one medical image based on the identification information; and generating an image series that includes the at least one patient image and the at least one medical image.

15. The computer-readable storage medium according to claim 14, wherein the identification information includes at least one of an identifier for the medical imaging device that acquires the at least one medical image, image information, image practitioner information, or patient information.

16. The computer-readable storage medium according to claim 14, further comprising:
receiving a plurality of different medical images based on the identification information for each medical image, wherein the identification information for each medical image includes an acquisition time within a specific time period and an identifier for the recording device on which the each medical image is recorded; and
comparing the plurality of different medical images to the at least one patient image; and
determining one or more medical images from the plurality of different medical images that corresponds to the at least one patient image based on the identifier for the recording device and the acquisition time.

17. The computer-readable storage medium according to claim 14, wherein the at least one patient image includes a portion of a body of the patient.

18. A system for generating an image series, comprising:
an image-activated circuitry to transmit an identifier associated with a medical imaging recording device when the image-activated circuitry detects a medical imaging device is triggered to acquire at least one medical image of a patient;
a camera to acquire at least one facial image of the patient when the medical imaging device is triggered to acquire the at least one medical image of the patient;
a memory; and
at least one processor, wherein the processor is configured to cause:
receive the at least one medical image of the patient acquired by the medical imaging device and recorded onto the recording device and identification information associated with the at least one medical image, the identification information including an acquisition time of the at least one medical image and an identifier for the recording device;
receive the at least one facial image of the patient acquired by the camera and identification information associated with the at least one patient image, the identification information including an acquisition time of the at least one facial image and the identifier for the recording device;
associate the at least one facial image and the at least one medical image based on the identification information; and
generate an image series including the at least one facial image and the at least one medical image.

19. The system according to claim 18, wherein the identification information includes at least one of an identifier for the medical imaging device that acquires the at least one medical image, image information, image practitioner information, or patient information.

20. The system according to claim 18, wherein the at least one facial image includes a portion of a body of the patient.

* * * * *